United States Patent [19]

Mifune et al.

[11] 4,272,614
[45] Jun. 9, 1981

[54] SILVER HALIDE PHOTOGRAPHIC LIGHT-SENSITIVE MATERIAL

[75] Inventors: Hiroyuki Mifune; Shigeo Hirano, both of Minami-ashigara, Japan

[73] Assignee: Fuji Photo Film Co., Ltd., Minami-ashigara, Japan

[21] Appl. No.: 105,689

[22] Filed: Dec. 20, 1979

[30] Foreign Application Priority Data

Dec. 28, 1978 [JP] Japan .................................. 54-82

[51] Int. Cl.$^3$ .............................................. G03C 1/06
[52] U.S. Cl. .................................... 430/441; 430/564; 430/600; 430/613; 430/614; 430/567; 430/627; 430/444; 430/448; 430/949; 430/266; 430/267
[58] Field of Search ............... 430/600, 627, 441, 444, 430/448, 567, 597, 598, 949, 564, 266, 267

[56] References Cited

U.S. PATENT DOCUMENTS

| 4,030,925 | 6/1977 | Leone et al. | 430/598 |
| 4,168,977 | 9/1979 | Takada et al. | 430/564 |

FOREIGN PATENT DOCUMENTS 53-16623 2/1978 Japan ...................................... 430/564

*Primary Examiner*—Won H. Louie, Jr.
*Attorney, Agent, or Firm*—Sughrue, Rothwell, Mion, Zinn and Macpeak

[57] ABSTRACT

A silver halide photographic light-sensitive material having at least one silver halide photographic emulsion layer comprising substantially surface latent image type silver halide grains, and containing in said photographic emulsion layer or at least one of other hydrophilic colloid layers a compound represented by the following general formula (I):

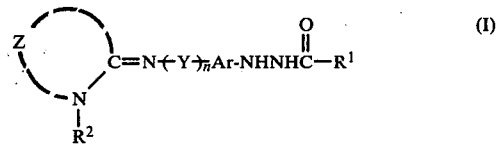

wherein $R^1$ represents a hydrogen atom, an aliphatic group which may be substituted or an aromatic group which may be substituted; Ar represents a divalent aromatic group which may be substituted; Y represents a divalent linking group; n represents 0 or 1; $R^2$ represents a hydrogen atom, an aliphatic group which may be substituted or an aromatic group which may be substituted; and Z represents a nonmetallic atomic group necessary to form a 5-membered or 6-membered heterocyclic ring together with the

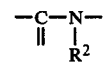

linkage.

30 Claims, No Drawings

SILVER HALIDE PHOTOGRAPHIC LIGHT-SENSITIVE MATERIAL

BACKGROUND OF THE INVENTION

1. Field of the Invention

This invention relates to a silver halide photographic light-sensitive material and, more particularly, to a silver halide photographic light-sensitive material providing photographic characteristics of extremely high contrast negative gradation.

2. Description of the Prior Art

U.S. Pat. No. 2,419,975 teaches that high contrast negative photographic characteristics can be obtained by adding a hydrazine compound to a silver halide photographic emulsion. This patent describes that extremely high contrast photographic characteristics, such as a gamma ($\gamma$) of more than 10, are obtained by adding a hydrazine compound to a silver bromochloride emulsion and developing with a developer having a pH value as high as 12.8. However, strongly alkaline developers having pH value near 13 are susceptible to oxidation by air and are therefore too unstable to be stored for a long period of time.

Super-high contrast photographic characteristics of more than 10 in gamma are extremely useful for the photographic reproduction of images with continuous gradation employing a dot image-forming process which is useful for making printing plates or for reproduction of line images, irrespective of whether the images are negative or positive. For the purpose of obtaining such photographic characteristics, a silver chlorobromide emulsion containing more than 50 mol% and preferably more than 75 mol% silver chloride has been used and developed with a hydroquinone-containing developer having an extremely reduced concentration of effective sulfite ion (usually 0.1 mol/l or less). However, such developer is very unstable due to its low sulfite ion concentration and cannot be stored longer than three days.

In addition, the above-described processes all require a silver chlorobromide emulsion containing silver chloride in a comparatively high content and hence high sensitivity cannot be obtained. Thus, it has been eagerly desired to obtain super-high contrast photographic characteristics useful for the reproduction of dot images or line images using a highly sensitive emulsion and a stable developer.

We have previously disclosed silver halide photographic emulsions permitting extremely high contrast negative photographic characteristics using a stable developer in Japanese Patent Application (OPI) Nos. 16623/78, 20921/78 (corresponding to U.S. Patent Application Ser. No. 967,541 filed on Dec. 7, 1978), 20922/78, etc. (The term "OPI" as used herein refers to a "published unexamined Japanese patent application".) However, the acylhydrazine compounds used therein have proved to possess some defects. One is that they undergo serious changes in sensitivity and gradation when the degree of stirring of the developer varies. Light-sensitive materials for use in printing are processed using an automatic developing machine or manual development (dish development). Usually, stirring conditions greatly differ depending upon the developing process and, in addition, stirring methods or stirring strength differ depending upon the type of automatic developing machine. Thus, differences in sensitivity and gradation result depending upon the manner in which the photographic materials are processed. Further, even in the same automatic developing machine, the stirring of the developer is not always uniform but varies from place to place within the developing machine and often results in uneven development when developing large sized film. Therefore, it has been strongly desired to obtain super-high contrast photographic light-sensitive materials which exhibit less variation in sensitivity and gradation and free from uneven development even when the developer stirring conditions vary and which are useful for the reproduction of dot images or line images.

SUMMARY OF THE INVENTION

An object of the present invention is to provide a silver halide photographic light-sensitive material which permits one to obtain an extremely high contrast negative image using a stable developer.

Another object of the present invention is to provide a silver halide light-sensitive material providing an extremely high contrast negative image, which exhibits less change in sensitivity and gradation and less unevenness of development due to changes in conditions such as stirring the developer.

These objects of the present invention are attained by a silver halide photographic light-sensitive material in which at least one silver halide photographic emulsion layer contains substantially surface latent image-forming type silver halide grains, and that photographic emulsion layer or at least one of the other hydrophilic colloid layers making up the material contains a compound represented by the following general formula (I):

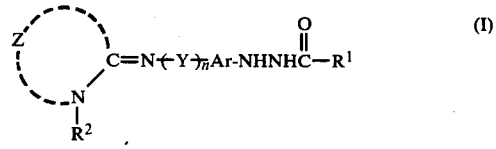

wherein $R^1$ represents a hydrogen atom, an aliphatic group which may be substituted or an aromatic group which may be substituted; Ar represents a divalent aromatic group which may be substituted; Y represents a divalent linking group; n represents 0 or 1; $R^2$ represents a hydrogen atom, an aliphatic group which may be substituted or an aromatic group which may be substituted; Z represents a non-metallic atomic group (comprising an atom such as C, O, S, Se, N, etc.) necessary to form a 5-membered or 6-membered heterocyclic ring together with the

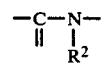

linkage.

DETAILED DESCRIPTION OF THE INVENTION

The aliphatic group represented by $R^1$ is preferably an aliphatic group having 1 to 8 carbon atoms and includes a straight or branched chain alkyl group (which may be substituted), a straight or branched chain alkenyl group (which may be substituted), a cycloalkyl group (which may be substituted), etc. The aromatic group represented by $R^1$ is preferably a mono or bicyclic aryl group which may be substituted.

Examples of the above substituents are preferably electron attracting groups, for example, a halogen atom (Cl, Br, I), a cyano group, a carboxyl group, a sulfo group, etc.

Specific examples of $R^1$ other than a hydrogen atom include a methyl group, an ethyl group, an n-propyl group, an isopropyl group, a trifluoromethyl group, a phenyl group, a 4-chlorophenyl group, a 4-bromophenyl group, a 4-carboxyphenyl group, a 4-sulfophenyl group, a 3,5-dichlorophenyl group, a 2,5-dichlorophenyl group, a 4-cyanophenyl group, etc. Of these, a hydrogen atom, a methyl group, and a phenyl group including a substituted phenyl group are preferred with a hydrogen atom being particularly preferred.

Specific examples of the divalent aromatic groups represented by Ar are a substituted or unsubstituted phenylene group (for example, a m-phenylene group, a p-phenylene group) or a substituted or unsubstituted naphthylene group. Representative substituents for the divalent aromatic group represented by Ar include, for example, an alkyl group containing 1 to 20 carbon atoms (which may be branched chain), a mono or bicyclic aralkyl group containing 1 to 3 carbon atoms in an alkyl moiety thereof (preferably having a total of 7 to 13 carbon atoms), an alkoxy group (preferably containing 1 to 20 carbon atoms), an amino group mono or di-substituted by an alkyl group (containing 1 to 20 carbon atoms), an aliphatic acylamino group (preferably containing 2 to 21 carbon atoms), an aromatic acylamino group (preferably containing 7 to 12 carbon atoms) an alkylthio group (preferably containing 1 to 12 carbon atoms), a hydroxy group, etc.

The most preferred Ar is a p-phenylene group.

The aliphatic group represented by $R^2$ includes a straight chain or branched chain alkyl group (for example, an alkyl group having 1 to 20 carbon atoms, such as a methyl group, an ethyl group, a butyl group, etc.), a cycloalkyl group (for example, a cycloalkyl group having 3 to 10 carbon atoms, such as a cyclopentyl group, a cyclohexyl group, etc.), a substituted alkyl group (preferably containing 1 to 20 carbon atoms), a substituted cycloalkyl group (preferably containing 3 to 10 carbon atoms), an alkenyl group (for example, an alkenyl group having 3 to 12 carbon atoms, such as an allyl group, etc.), an alkynyl group (for example, an alkynyl group having 2 to 10 carbon atoms, such as an acetylene group, etc.), etc.

The aromatic group represented by $R^2$ is preferably a mono or bicyclic aryl group which may be substituted (more preferably, having 6 to 10 carbon atoms).

The above mentioned substituents preferably have up to 15 carbon atoms or have no carbon atom, for example, an alkoxy group (for example, a methoxy group, an ethoxy group, etc.), an aryl group (for example, a phenyl group, etc.), an alkylthio group (for example, an ethylthio group, etc.), an aliphatic or aromatic acylamino group (for example, an acetamido group, a benzamido group, etc.), an aliphatic or aromatic acyloxy group (for example, an acetoxy group, a benzoyloxy group, etc.), an alkoxycarbonyl group (for example, a methoxy carbonyl group, etc.), a mercapto group, a sulfo group or salt thereof, a carboxy group or salt thereof, a hydroxy group, a halogen atom (for example, a chlorine atom, a bromine atom, an iodine atom, etc.), an amino group, an alkylamino group (for example, a dimethylamino group, etc.), and a carbamoyl group, etc.

Specific examples of the divalent linking group represented by Y are $-X-R^3-CONH-$ and $-X-R^3-SO_2NH-$ wherein X represents a divalent aromatic group which such as defined for Ar (for example, a phenyl group, a substituted phenyl group, a naphthyl group, a substituted naphthyl group, etc.) or a saturated or unsaturated divalent aliphatic group having preferably 1 to 6 carbon atoms (for example, an alkylene or alkenylene group, such as an ethylene group, a butylene group, a butenylene group, etc.).

$R^3$ represents $-A-R^4$ wherein A represents $-O-$, $-S-$,

or a direct bond, $R^4$ represents a saturated or unsaturated divalent aliphatic group having preferably 1 to 6 carbon atoms (for example, an alkylene or alkenylene group, such as an ethylene group, a butylene group, a butenylene group, etc.) or a direct bond. $R^5$ represents an aliphatic group having preferably 1 to 6 carbon atoms (for example, an alkyl group which may be substituted, a cycloalkyl group which may be substituted, etc.) or an aromatic group having preferably 6 to 12 carbon atoms (for example, a mono or bicyclic aryl group, such as a phenyl group, a naphthyl group, etc.).

The heterocyclic ring formed by Z can be condensed with an aromatic ring such as a benzene ring or a naphthalene ring or an aliphatic ring such as a cyclopentene ring or a cyclohexene ring and can be substituted. Specific examples of the heterocyclic rings include a thiazoline ring, a benzothiazoline ring, naphthothiazoline ring, a thiazolidine ring, an oxazoline ring, a benzoxazoline ring, an oxazolidine ring, a selenazoline ring, a benzoselenazoline ring, an imidazoline ring, a benzimidazoline ring, a tetrazoline ring, a triazoline ring, a thiadiazoline ring, an 1,2-dihydropyridine ring, an 1,2-dihydroquinoline ring, an 1,2,3,4-tetrahydroquinoline ring, a perhydro-1,3-oxazine ring, a 2,4-benz[d]-oxazine ring, a perhydro-1,3-thiazine ring, a 2,4-benzo[d]-thiazine ring, an uracil ring, etc.

The substituents for these heterocyclic rings preferably have up to 18 carbon atoms or no carbon atom, for example, an alkyl group (e.g., a methyl group, an ethyl group, etc.), an alkoxy group (e.g., a methoxy group, an ethoxy group, etc.), an alkylthio group (e.g., a methylthio group, a propylthio group, etc.), a hydroxy group, a sulfo group, a cyano group, a halogen atom, a carboxy group, an amino group, a nitro group, an oxo group, a thioxo group, an alkylidene group (e.g., a propylidene group, etc.), an aralkylidene group (e.g., a benzilidene group, etc.).

Although the function of the compound represented by the general formula (I) is not absolutely clear, the compound does not act as a halogen acceptor as described in T. H. James, *The Theory of the Photographic Process,* 4th Edition, page 158 (Macmillan Co.) because the compound does not yield its effect when the compound is present only during exposure. Further, the compound does not act as a developing agent because the light-sensitive material of the present invention does not form images without a developing agent as demonstrated below. The compound according to the present invention can increase the sensitivity of light-sensitive materials and provide super-high contrast images when the compound is present upon development.

Specific examples of the compounds of the present invention represented by the general formula (I) are as follows. These examples are not to be construed as limiting.

1. 1-Formyl-2-[4-(3-methylbenzothiazolin-2-ylidenamino)phenyl]hydrazide
2. 1-Acetyl-2-[4-(3-methylbenzothiazolin-2-ylidenamino)phenyl]hydrazide
3. 1-Benzoyl-2-[4-(3-methylbenzothiazolin-2-ylidenamino)phenyl]hydrazide
4. 1-Formyl-2-[3-(3-propylbenzothiazolin-2-ylidenamino)phenyl]hydrazide
5. 1-Formyl-2-{4-[3-(2-mercaptoethyl)benzothiazolin-2-ylidenamino]phenyl}hydrazide
6. 1-Formyl-2-{4-[3-(3-mercaptopropyl)benzothiazolin-2-ylidenamino]phenyl}hydrazide
7. 2-{4-[3-(2-Carboxyethyl)benzothiazolin-2-ylidenamino]phenyl}-1-formylhydrazide
8. 1-Formyl-2-{4-[3-(2-sodium sulfonatoethyl)benzothiazolin-2-ylidenamino]phenyl}hydrazide
9. 1-Formyl-2-{4-[3-(3-sodium sulfonatopropyl)benzothiazolin-2-ylidenamino]phenyl}hydrazide
10. 1-Formyl-2-[4-(3-methylthiazolin-2-ylidenamino)phenyl]hydrazide
11. 1-Formyl-2-[4-(3-methylthiazolidin-2-ylidenamino)phenyl]hydrazide
12. 2-[4-(3-Ethylthiazolidin-4-one-2-ylidenamino)phenyl]-1-formylhydrazide
13. 2-[4-(5-benzylidene-3-methylthiazolidin-4-one-2-ylidenamino)phenyl9 -1-formylhydrazide
14. 1-Formyl-2-[4-(3-methylbenzoxazolin-2-ylidenamino)phenyl]hydrazide
15. 1-Formyl-2-[4-(3-methylbenzoselenazolin-2-ylidenamino)phenyl]hydrazide
16. 1-Formyl-2-[4-(1,3-dimethylbenzimidazolin-2-ylidenamino)phenyl]hydrazide
17. 1-Formyl-2-[4-(3-methyl-1,3,4-thiadiazolin-2-ylidenamino)phenyl]hydrazide
18. 1-Formyl-2-[4-(1-methyl-1,2-dihydropyridin-2-ylidenamino)phenyl]hydrazide
19. 2-[4-(1-Benzyl-1,2-dihydroquinolin-2-ylidenamino)phenyl]-1-formylhydrazide
20. 2-[4-(3-Cyclohexylperhydro-1,3-oxazin-2-ylidenamino)phenyl]-1-formylhydrazide
21. 1-Formyl-2-[4-(4-methyl-2,4-benzo[d]thiazin-2-ylidenamino)phenyl]hydrazide
22. 1-Formyl-2-{4-[3-(3-methylbenzothiazolin-2-ylidenamino)benzamide]phenyl}hydrazide
23. 1-Formyl-2-{4-[3-(3-methylbenzothiazolin-2-ylidenamino)benzenesulfonamido]phenyl}hydrazide
24. 1-Formyl-2-[4-{2-[4-(3-methylbenzothiazolin-2-ylidenamino)phenoxy]acetamido}phenyl]hydrazide The compound represented by the general formula (I) used in the present invention can generally be synthesized by condensing a nitrogen-containing heterocyclic quaternary ammonium salt (III) having a releasable group (L) such as an alkylthio group or a halogen atom with an amino compound (IV) having an acylhydrazido group in the presence of an appropriate basic condensating agent (for example, trialkylamine, pyridine, sodium hydrogen carbonate, in the manner shown by the following reaction scheme:

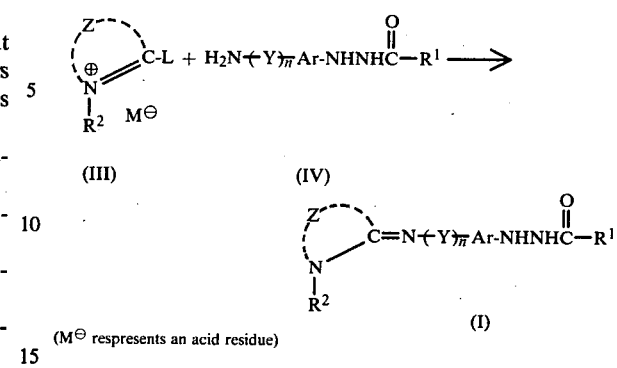

($M^\ominus$ respresents an acid residue)

Examples of the condensation reaction described above are described, for example, in *J. Chem. Soc.*, page 470 (1939), ibid., page 1716 (1951), ibid., page 907 (1937), *J. Amer. Chem. Soc.*, Vol. 64, page 199 (1942), ibid. Vol. 63, page 3192 (1941), etc.

The amino compound (IV) having an acylhydrazido group (for example, 2-(4-aminophenyl)-1-formylhydrazide, 1-formyl-2-{4-[2-(3-aminophenoxy)acetamido]phenyl}hydrazide) which is a starting material may be synthesized by the method described in Japanese Patent Application (OPI) No. 133126/79 (corresponding to U.S. Patent Application Ser. No. 26,962 filed on April 4, 1979).

In general, the above amino compound (IV) can be obtained by the following method. By reacting 4- or 3-nitrophenyl-hydrazine with formic acid or a corresponding acid anhydride or acid chloride, 1-formo-2-(4- or 3-nitrophenyl)hydrazine or the corresponding 1-acylo-2-(4- or 3-nitrophenyl)hydrazine can be obtained. By catalytically reducing the 1-formo- or 1-acylo-2-(4- or 3-nitrophenyl)hydrazine with hydrogen gas in a solvent such as an alcohol (e.g., ethanol, methyl cellosolve, etc.) ior a dioxane, in the presence of palladium-carbon as a catalyst or by heating the 1-formo- or 1-acylo-2-(4- or 3-nitrophenyl)hydrazine with reduced iron in an alcohol, the corresponding 1-formo- or 1-acylo-2-(4- or 3-aminophenyl)hydrazine can be obtained with ease.

Synthesis of the nitrogen-containing heterocyclic quaternary ammonium salt compound (III) having a releasable group L was carried out in the manner described, for example, in *Heterocyclic Compound*, Vol. 5, page 484 (1967), compiled by R. C. Elderfield (published by John Wiley and Son Inc.), *J. Amer. Chem. Soc.*, Vol. 64, page 199 (1942), ibid., Vol. 63, page 3192 (1941), *J. Chem. Soc., page* 143 (1939), Japanese Patent Publication Nos. 44337/77 and 39615/77, etc.

Compound (III) and Compound (IV) are reacted at a concentration of about 0.1 mol/l to 10 mol/l each in a molar ratio of Compound (III): Compound (IV) of about 1:1 to 1:1.5, preferably about 1:1. The temperature of the reaction is about 15° C. to 100° C., preferably about 40° C. to to 50° C. It is preferred to provide an almost neutral pH when the reaction is completed, but it is not preferred that the pH range is too high. Synthesis examples of the compounds according to the present invention are specifically set forth below.

1. Synthesis of Compound 1

15.1 g of 2-(4-aminophenyl)-1-formylhydrazide and 36.8 g of 3-methyl-2-methylthiobenzothiazoliummethanesulfonate were dispersed in 250 ml of acetonitrile and to the mixture, 13 ml of triethylamine was added dropwise at room temperature (25° C.) with stirring.

After refluxing under heating for 2 hours, 300 ml of water was added to the reaction mixture and the crude crystals were collected by filtration. By recrystallization from a solvent mixture of dimethylformamide and ethylacetate, 15 g of the objective compound was obtained. Melting Point: 221° and 223° C. (decomposition).

2. Synthesis of Compound 5

To a solution containing 10.6 g of 2-(4-aminophenyl)-1-formylhydrazide and 15 g of pyridine in a mixture of methanol and water (150 ml/150 ml), 17.4 g of 2,3-dihydrothiazole[2,3-b]benzothiazolium bromide was added to room temperature (25° C.). After further stirring at room temperature for 3 hours, the crude crystals were collected by filtration and dissolved in 80 ml of dimethylformamide. To the solution, 240 ml of methanol was added and the crystals thus precipitated were collected by filtration followed by washing with methanol. 17.5 g of the objective compound having a melting point of 194.5° to 197° C. (decomposition) was obtained.

3. Synthesis of Compound 12

To a mixture of 25 g of 2-(4-aminophenyl)-1-formylhydrazide and 200 ml of ethanol, 16.7 g of ethylisothiocyanate was added dropwise at room temperature (25° C.) and the mixture was stirred at 55° C. for 1 hour. After adding 21 g of triethylamine, 20.7 g of ethyl chloroacetate was added dropwise to the mixture for 20 minutes. The mixture was reacted for 2 hours while refluxing under heating. After cooling, 800 ml of water was added to the mixture and the crystals precipitated were collected by filtration. The crystals were crystallized from methanol to obtain 28.5 g of the objective compound. Melting Point: 184° to 185° C. (decomposition).

In the case of incorporating the compound of the present invention represented by the general formula (I) in a photographic light-sensitive material, it can be incorporated in one or more of the hydrophilic colloid layers of the light-sensitive material. It may be added to photographic light-sensitive emulsion layers or to other non-light-sensitive layers such as a protective layer, inter-layer, filter layer, antihalation layer, etc. Preferably, it is incorporated in a surface latent image type silver halide photographic emulsion layer. However, the compound can be added to other types of silver halide emulsion layers. Also it can be added to one emulsion layer or two or more layers.

The compound of the formula (I) is incorporated in the light-sensitive material in an amount of about $10^{-8}$ mol to $10^{-2}$ mol, preferably about $10^{-6}$ to $10^{-3}$ mol, per mol of silver halide in the light-sensitive material. An optimal amount of the compound depends upon the grain size of the silver halide emulsion, the halide composition, the process and the degree of chemical sensitization, the relation between the layer containing the compound and the photographic emulsion layers, the anitfogging agent, and the like. Testing methods for the selection of an optimum amount are well known and do not require an undue amount of experimentation.

In order to incorporate the compound of the general formula (I) in silver halide emulsion layers or other nonlight-sensitive hydrophilic colloid layers, the compound is added to photographic emulsions or coating solutions of nonlight-sensitive layers. Specifically, the compound is added to a hydrophilic colloid solution as a solution of a water-miscible organic solvent such as an alcohol (e.g., methanol, ethanol, etc.), an ester (e.g., ethyl acetate, etc.), a ketone (e.g., acetone, etc.), or the like; or, when the compound is water-soluble, as an aqueous solution.

In the case of adding the compound to a photographic emulsion, the addition may be conducted at any stage from initiation of chemical ripening to proir to coating but, preferably, it is conducted after completion of chemical ripening. In particular, addition to a solution which is otherwise ready for coating is preferred.

The compound of the formula (I) according to the present invention has the advantage that it has a remarkably high activity and thus the amount used can be small, and further in that it does not affect to the photographic characteristics under a condition of high temperature and high humidity.

In the present invention, silver halide grains used in at least one silver halide emulsion layer are preferably substantially surface latent image type grains. The term "substantially surface latent image type" as used herein means that when developed a light-sensitive material which does not contain a compound represented by the general formula (I) of the present invention according to surface-developing process (A) and internally developing process (B) described below, after exposure for 1 to 1/100 second, the sensitivity obtained by surface development (A) is greater than that obtained by internal development (B).

Sensitivity as used herein is defined as follows:

$$S = (100/Eh)$$

wherein S represents sensitivity, and Eh represents the exposure amount necessary for obtaining a density just intermediate maximum density ($D_{max}$) and minimum density ($D_{min}$) [i.e., $\frac{1}{2}(D_{max} + D_{min})$].

Surface Development (A)

Development for 10 minutes at 20° C. in a developer having the following formulation.
N-Methyl-p-aminophenol (hemisulfate): 2.5 g
Ascorbic Acid: 10 g
Sodium Metaborate Tetrahydrate: 35 g
Potassium Bromide: 1 g
Water to make: 1 l Internal Development (B)

Treatment for 10 minutes at about 20° C. in a bleaching solution containing 3 g/l potassium ferricyanide and 0.0125 g/l phenosafranine, then development for 10 minutes at 20° C. in a developer having the following formulation after washing with water for 10 minutes.
N-Methyl-p-aminophenol (hemisulfate): 2.5 g
Ascorbic Acid: 10 g
Sodium Metaborate Tetrahydrate: 35 g
Potassium Bromide: 1 g
Sodium Thiosulfate: 3 g
Water to make: 1 l As silver halide, any of silver chloride, silver chlorobromide, silver chlorobromoiodide, silver bromide, and silver bromoiodide can be used. With silver bromoiodide or silver chlorobromoiodide, the content of silver iodide is preferably not more than 10 mol%. Since the process of the present invention enables the use of such a wide variety of silver halides, much higher sensitivity can be obtained as compared with conventional processes using "lith" type development.

The photographic emulsion used in the present invention can be prepared according to the processes described in P. Glafkides, *Chimie et Physique Photogra-*

*phique* (published by Paul Montel in 1967), G. F. Duffin, *Photographic Emulsion Chemistry* (The Focal Press, 1966), V. L. Zelikman et al., *Making and Coating Photographic Emulsion* (published by The Focal Press in 1964), etc. That is, silver halide emulsions prepared according to any of an acid process, neutral process, and ammoniacal process may be used.

As the manner of reacting a soluble silver salt with a soluble halide, any of a one-side mixing process, a simultaneously mixing process, or combinations thereof, etc., may be employed. It is also possible to employ the process of forming grains in the presence of excess silver ion (a so-called reverse-mixing process). As one of the simultaneously mixing processes, a process of maintaining pAg of the liquid phase, in which silver halide is formed, at a constant level, i.e., so-called controlled double jet process, can be used. This process provides a silver halide emulsion containing silver halide grains having a regular crystal form and an approximately uniform particle size.

Silver halide grains in the photographic emulsion used in the present invention may have a comparatively broad grain size distribution but, preferably, have a narrow grain size distribution. Particularly preferably, 90% (by weight or number) of the total silver halide grains are within ±40% of the mean grain size. Such emulsions are generally called monodisperse emulsions. The mean particle size of the silver halide grains used in the present invention is not particularly limited but, preferably, it is not greater, than 0.7μ. The method for determining the mean particle size is described in detail in C. E. K. Mees & T. H. James, *The Theory of the Photographic Process*, 3rd Ed., pp. 36–53 (published by Macmillan Co. in 1966).

A mean particle size of not more than 0.4μ is more preferred in the present invention. The process of the present invention is characterized in that it provides high sensitivity in spite of the small mean particle size of the silver halide grains.

The silver halide grains in the photographic emulsion may be regular crystals such as cubic or octahedral crystals, or irregular crystals such as spherical or plate-like crystals as well as mixed forms thereof. Further, they may comprise a mixture of grains which various crystal forms. The inner part and exterior part of the silver halide grains may be different phases or they may comprise a single homogeneous phase. Two or more silver halide emulsions separately prepared may also be mixed and used.

As the binder or protective colloid for the photographic emulsion, gelatin is advantageously used. Also, other hydrophilic colloids can be used. For example, there can be used gelatin derivatives; graft polymers of gelatin and other high polymers; proteins such as albumin, casein, etc.; cellulose derivatives such as hydroxyethyl cellulose, carboxymethyl cellulose, cellulose sulfate, etc.; sugar derivatives such as sodium alginate, starch derivatives, etc.; various synthetic and hydrophilic homo- or copolymers such as polyvinyl alcohol, partly acetallized polyvinyl alcohol, poly-N-vinyl pyrrolidone, polyacrylic acid, polymethacrylic acid, polyacrylamide, polyvinylimidazole, polyvinylpyrazole, etc.

As the gelatin, acid-processed gelatin may be used as well as lime-processed gelatin. Further, hydrolyzates or enzyme-decomposed products of gelatin may be used. As gelatin derivatives, those obtained by reacting gelatin with various compounds such as acid halides, acid halides, acid anhydrides, isocyanates, bromoacetic acid, alkanesultones, vinylsulfonamides, maleinimides, polyakylene oxides, epoxy compounds, etc., may be used. Specific examples thereof are described in U.S. Pat. Nos. 2,614,928, 3,132,945, 3,186,846, 3,312,553, British Pat. Nos. 861,414, 1,033,189, 1,005,784, Japanese Patent Publication No. 26845/67, etc.

As examples of aforesaid gelatin graft polymer, those prepared by grafting to gelatin a mono- or copolymer of vinyl series monomer such as acrylic acid, methacrylic acid, the derivative thereof such as the esters or amides, acrylonitrile, styrene, etc., may be used. Of these, graft polymers with a polymer having a compatibility with gelatin to some extent such as a polymer of acrylic acid, methacrylic acid, acrylamide, methacrylamide, hydroxyalkyl methacrylate, etc., are preferred. Examples thereof are described in U.S. Pat. Nos. 2,763,625, 2,831,767, 2,956,884, etc.

Typical synthetic hydrophilic high molecular materials are described in, for example, West German Patent Application (OLS) No. 2,312,708, U.S. Pat. Nos. 3,620,751, 3,879,205, and Japanese Patent Publication No. 7561/68.

The silver halide emulsion used in the present invention preferably does not contain more than 250 g binder per mol of silver halide. Where the silver halide emulsion contains not more than 250 g binder per mol of silver halide, extremely high contrast photographic characteristics which are the object of the present invention can be obtained more easily.

The emulsion is usually subjected to the step of removing soluble salts after formation of the precipitate or physical ripening. Noodle washing method which is well known and conducted following gelation, or a flocculation method utilizing an inorganic salt comprising polyvalent anion such as sodium sulfate, an anionic surfactant, an anionic polymer (e.g., polystyrenesulfonic acid, etc.), or a gelatin derivative (e.g., aliphatically acylated gelatin, aromatically acylated gelatin, aromatically carbamoylated gelatin, etc.) may be employed for the purpose. This step of removing soluble salts may be omitted.

The silver halide emulsion used in the present invention is preferably chemically sensitized but may not be. As methods for chemically sensitizing silver halide emulsion, there are known sulfur sensitization, reduction sensitization, and noble metal sensitization, and any of these may be used alone or in combination. These methods are described in the aforesaid books by Glafkides or by Zelikman et al, or in *Die Grundlagen der photographischen Prozesse mit Silberhalogeniden* compiled by H. Frieser (Akademische Verlagsgesellschaft, 1968).

Of the noble metal-sensitizing methods, a gold-sensitizing method is typical which uses gold compounds, mainly gold complexes. Complexes of other noble metals than gold such as platinum, palladium, iridium, etc., may be used as well. Specific examples are described in U.S. Pat. No. 2,448,060, British Pat. No. 618,061, etc.

As the sulfur sensitizing agents, there can be used various sulfur compounds such as thiosulfates, thioureas, thiazoles, rhodanines, etc., as well as sulfur compounds contained in gelatin. Specific examples are described in U.S. Pat. Nos. 1,574,944, 2,278,947, 2,410,689, 2,728,668, 3,501,313, 3,656,955, etc.

As the reduction sensitizing agents, there can be used stannous salts, amines, formamidinesulfinic acid silane compounds, etc. Specific examples thereof are described in U.S. Pat. Nos. 2,487,850, 2,518,698, 2,983,609, 2,983,610, and 2,694,637.

In the light-sensitive material of the present invention, various compounds for preventing fog or stabilizing the photographic characteristics during production steps, storage, or photographic processing of the light-sensitive material may be incorporated. Many compounds known as anti-fogging or stabilizing agents such as azoles (e.g., benzothiazolium salts, nitroindazles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (particularly, 1-phenyl-5-mercaptotetrazole), etc.); mercaptopyrimidines; mercaptotriazines; thioketo compounds (e.g., oxazolinethione, etc.); azaindenes (e.g., triazaindenes, tetrazaindenes (particularly, 4-hydroxy-substituted 1,3,3a,7-tetrazaindenes, etc.), pentazaindenes, etc.); benzenethiosulfonic acid; benzenesulfonic acid; benzenesulfonamide; etc. may be added. Of these, benzotriazoles (e.g., 5-methylbenzotriazole) are particularly preferred. These compounds may be incorporated in a processing solution.

Addition of a small amount of iodide (e.g., potassium iodide) to the emulsion after formation of the grains, before or after chemical ripening, or before coating enhances the effects of the present invention. Such iodides are suitably added in an amount of about $10^{-4}$ to $10^{-2}$ mol/mol Ag.

The light-sensitive material used in the present invention may contain sensitizing dyes (for example, cyanine dyes, merocyanine dyes, etc.) any of which may be used alone or in combination, super-sensitizing agents (for example, aminostilbene compounds, aromatic organic acid-formaldehyde condensates, cadmium salts, azaindene compounds, etc.), water-soluble dyes (for purposes like filter or anti-irradiation, for example, oxonol dyes, hemioxonol dyes, merocyanine dyes, etc.), hardeners (for example, chromium salts, aldehydes, N-methylol compounds, dioxane derivatives, active vinyl compounds, active halogen compounds, etc.), surface active agents (for example, various known nonionic, anionic, cationic or amphoteric surface active agents.

The light-sensitive material of the present invention may contain a dispersion of water-insoluble or slightly soluble synthetic polymer for the purpose of improving dimensional stability, etc. For example, there can be used homo- or copolymers of alkyl (meth)acrylates, alkoxyalkyl (meth)acrylates, glycidyl (meth)acrylate, (meth)acrylamide, vinyl ester (e.g., vinyl acetate), acrylonitrile, olefins, styrene, etc., or polymers containing as monomer components combination of the above-described ones and acrylic acid, methacrylic acid, α,β-unsaturated dicarboxylic acid, hydroxyalkyl (meth)acrylate, sulfoalkyl (meth)acrylate, styrenesulfonic acid, or the like. As such polymers, there can be used, for example, those described in U.S. Pat. Nos. 2,376,005, 2,739,137, 2,853,457, 3,062,674, 3,411,911, 3,488,708, 3,525,620, 3,607,290, 3,635,715, 3,645,740, British Pat. Nos. 1,186,699, 1,307,373, etc. High contrast emulsions as in the present invention are suited for reproduction of line images and, since dimensional stability is of importance in such use, incorporation of the above-described polymer dispersion is preferred.

In the process of the present invention, imagewise exposed silver halide photographic light-sensitive materials can be photograhically processed in a conventional manner.

Processing solutions can be conventional except the developer. Either of development processing forming only silver images (black-and-white photographic processing) or color photographic processing comprising development processing forming dye images may be used depending on the end use. Processing temperature is usually selected from between 18° C. and 50° C., but temperatures of lower than 18° C. or higher than 50° C. may also be employed.

In the case of black-and-white photographic processing, the developer can contain known developing agents. As such compounds, there are illustrated 3-pyrazolidones (e.g., 1-phenyl-3-pyrazolidone), aminophenols (e.g., N-methyl-p-aminophenol, etc.), 1-phenyl-3-pyrazoline, dihydroxybenzenes, (e.g., hydroquinone, etc.), etc. The compounds may be used in combination. In particular, developers containing dihydroxybenzenes (especially hydroquinone) are preferred. The developer containing a dihydroxybenzene (especially hydroquinone) as a sole developing agent is particularly preferred.

The silver halide photographic material of the present invention is preferably developed in the presence of a polyalkylene oxide having a molecular weight at least about 600. The polyalkylene oxide may be employed either in the silver halide photographic material or in the developer.

The polyalkylene oxide compounds used in the present invenion include condensates between polyalkylene oxides comprising at least 10 units of an alkylene oxide having 2 to 4 carbon atoms, such as ethylene oxide, propylene-1,2-oxide, butylene-1,2-oxide, preferably ethylene oxide, and compounds having at least one active hydrogen atom such as water, aliphatic alcohols, aromatic alcohols, phenols, fatty acids, organic amides, organic amines, hexitol derivatives, etc., and block copolymers of two or more polyalkylene oxides. More specifically, suitable polyalkylene oxide compounds which can be used include polyalkylene glycols, polyalkylene glycol alkyl ethers, polyalkylene glycol aryl ethers, polyalkylene glycol alkylaryl ethers, polyalkylene glycol esters, polyalkylene glycol fatty acid amides, polyalkylene glycol amines, polyalkylene glycol block copolymers, polyalkylene glycol graft polymers, etc.

Suitable aliphatic alcohols and aromatic alcohols which can be used can be represented by the general formulae (V), (VI) and (VII):

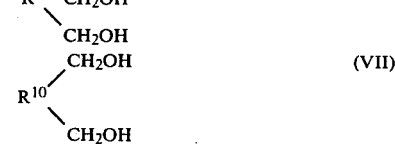

wherein $R^6$, $R^7$ and $R^8$, which may be the same or different, each represents a hydrogen atom, an alkyl group having 1 to 30 carbon atoms (e.g., $-CH_3$, $-C_2H_5$, $-C_3H_7$, $-C_{11}H_{23}$, $-C_{17}H_{35}$, $-C_{22}H_{45}$, etc.), an aryl group (e.g.,

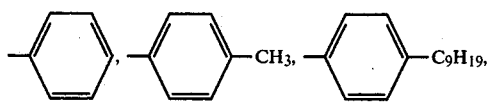

etc.) or an alkenyl group (e.g., $C_8H_{17}CH=CHC_7H_{14}-$); $R^9$ represents an alkantriyl group having 2 to 30 carbon atoms; and $R^{10}$ represents an alkandiyl group having 2 to 30 carbon atoms.

Suitable phenols which can be used can be represented by the general formulae (VIII) to (X).

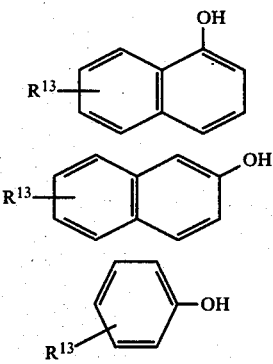

wherein $R^{13}$ represents a hydrogen atom, an alkyl group having 1 to 30 carbon atoms (e.g., $-CH_3$, $-C_2H_5$, $-C_3H_7$, $-C_9H_{19}$, $-C_{11}H_{23}$) or an alkenyl group (e.g., $C_8H_{17}CH=CHC_7H_{14}-$, etc.).

Suitable fatty acids which can be used can be represented by the general formulae (XI) and (XII):

$$R^{14}COOH \quad (XI)$$
$$R^{15}\begin{matrix}COOH\\ \\COOH\end{matrix} \quad (XII)$$

wherein $R^{14}$ represents an alkyl group having 1 to 30 carbon atoms (e.g., $-CH_3$, $-C_2H_5$, $-C_8H_{17}$, $-C_{11}H_{23}$, $-C_{17}H_{35}$, $-C_{22}H_{45}$, etc.) or an alkenyl group (e.g., $C_8H_{17}CH=CHC_7H_{14}-$); and $R^{15}$ represents an alkandiyl group having 2 to 30 carbon atoms.

Suitable organic amides which can be used can be represented by the general formula (XIII):

$$R^{16}CONH\overset{R^{17}}{|} \quad (XIII)$$

wherein $R^{16}$ represents an alkyl group having 1 to 30 carbon atoms (e.g., $-CH_3$, $-C_2H_4$, $-C_3H_7$, $-C_5H_{11}$, $-C_9H_{19}$, $-C_{11}H_{23}$, $-C_{17}H_{35}$, $-C_{22}H_{45}$, etc.) or an aryl group (e.g.,

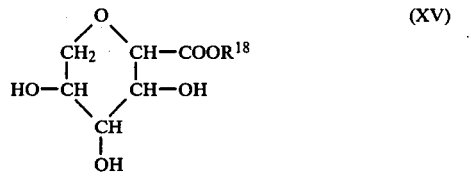

etc.) and $R^{17}$ represents a hydrogen atom, an alkyl group having 1 to 30 carbon atoms (e.g., $-CH_3$, $-C_2H_5$, $-C_3H_7$, $-C_5H_{11}$, $-C_9H_{19}$, $-C_{11}H_{23}$, $-C_{17}H_{35}$, $-C_{22}H_{45}$, etc.) or an aryl group (e.g.,

etc.).

Suitable organic amines which can be used can be represented by the general formula (XIV):

$$\begin{matrix}R^{16}\\ \phantom{R^{16}}\searrow\\ \phantom{R^{16}\searrow}NH\\ \phantom{R^{16}\searrow}\nearrow\\ R^{17}\end{matrix} \quad (XIV)$$

wherein $R^{16}$ and $R^{17}$ are the same as defined above for the general formula (XIII).

Suitable hexitol derivatives which can be used can be represented by the general formula (XV):

wherein $R^{18}$ represents an alkyl group having 1 to 30 carbon atoms (e.g., $-C_2H_5$, $-C_9H_{19}$, $-C_{11}H_{23}$, $-C_{17}H_{35}$, $-C_{22}H_{45}$, etc.) or an aryl group (e.g.,

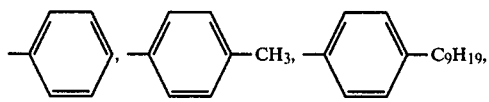

etc.).

The number of polyalkylene oxide chains is not limited and one, two or more chains may be present in the molecule. In such case, each polyalkylene oxide chain may contain less than 10 alkylene oxide units, but the sum of the akylene oxide units in the molecule must be at least 10. With compounds containing two or more polyalkylene oxide chains in the molecule, each polyalkylene oxide chain may contain the same alkylene oxide units or alkylene oxide units different from that of the other chain or chains. For example, one chain may comprise ethylene oxide units, and the other chain may comprise propylene oxide units. The polyalkylene oxide compounds used in the present invention preferably contain 14 to 100 alkylene oxide units.

Specific examples of polyalkylene oxide compounds which can be used in the present invention are described below.

Suitable examples of polyalkylene oxide compounds which can be used are those described in U.S. Pat. No. 4,011,082, Japanese Patent Application (OPI) No. 108130/77 (corresponding to U.S. Patent Application Ser. No. 775,682 filed on Mar. 8, 1977) and Japanese Patent Application (OPI) No. 3217/78, such as:

HO⁺CH₂CH₂O⁺₉₀H    PAO-(1)
C₄H₉O⁺CH₂CH₂O⁺₁₅H    PAO-(2)
C₁₂H₂₅O⁺CH₂CH₂O⁺₁₅H    PAO-(3)
C₁₈H₃₇O⁺CH₂CH₂O⁺₁₅H    PAO-(4)
C₁₈H₃₇O⁺CH₂CH₂O⁺₈₀H    PAO-(5)
C₈H₁₇CH=CHC₈H₁₆O⁺CH₂CH₂O⁺₁₅H    PAO-(6)

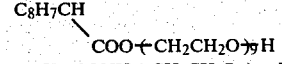    PAO-(7)

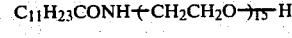    PAO-(8)

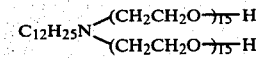    PAO-(9)

C₁₁H₂₃COO⁺CH₂CH₂O⁺₈₀H    PAO-(10)
C₁₁H₂₃COO⁺CH₂CH₂O⁺₂₄OCC₁₁H₂₃    PAO-(11)

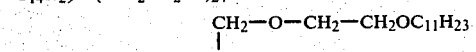    PAO-(12)

C₁₁H₂₃CONH⁺CH₂CH₂O⁺₁₅H    PAO-(13)

    PAO-(14)

    PAO-(15)

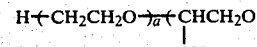    PAO-(16)

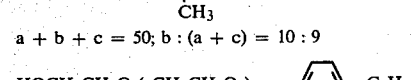

a + b + c = 50; b : (a + c) = 10 : 9

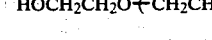    PAO-(18)

(CH₂CH₂O)₅₀H    PAO-(19)
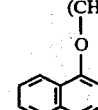

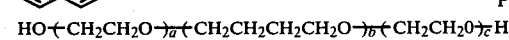    PAO-(20)

a + c = 30; b = 14

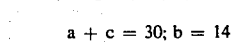    PAO-(21)

b = 8; a + c = 50

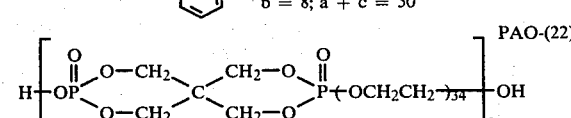    PAO-(22)

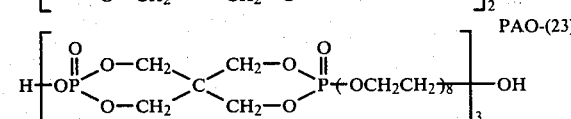    PAO-(23)

HO⁺CH₂CH₂O⁺₃₄H    PAO-(24)

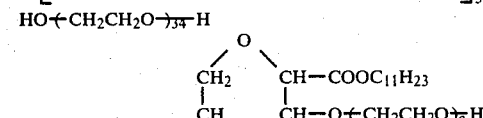    PAO-(25)

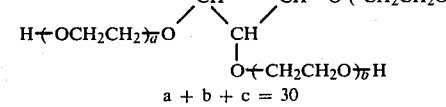

a + b + c = 30

In adding the polyalkylene oxide compound to a silver halide emulsion, it can be added as an aqueous solution of a suitable concentration or as an organic solution by dissolving the polyalkylene oxide compound in a water-miscible organic solvent having a low boiling point at an appropriate stage before coating, preferably after chemical ripening of the silver halide emulsion. The polyalkylene oxide compound may be added to a light-insensitive hydrophilic colloid layer such as an interlayer, a protective layer, a filter layer, etc. instead of the silver halide emulsion, if desired.

In addition, in adding the above-described polyalkylene oxide compound to a developer, it can be added to the developer as a solid or as an aqueous solution of a suitable concentration, or by dissolving the polyalkylene oxide compound in a water-miscible low-boiling organic solvent.

A suitable amount of the polyalkylene oxide compound used in the present invention when employed in the light-sensitive material is about $5 \times 10^{-4}$ g to 5 g, preferably $1 \times 10^{-3}$ g to 1 g, per mol of silver halide.

A suitable amount of the polyalkylene oxide compound used in the present invention when employed in a developer is about $1 \times 10^{-2}$ g or more, preferably $5 \times 10^{-2}$ g to 40 g, per liter of the developer.

In addition, the developer generally contains a known preservative, alkali agent, pH buffering agent, anti-fogging agent, etc., and, if necessary, it may contain a dissolving aid, toning agent, development accelerator, surface active agent, defoaming agent, water softener, hardening agent, viscosity-imparting agent, etc.

The process of the present invention enables one to obtain gamma higher than 10 even when developing with a developer containing not less than about 0.15 mol/l sulfite ion. The pH of the developer to be used in the process of the present invention is suitably above about 10, preferably about 10.5 to 12.3. If the pH exceeds 12.3, the developer becomes so unstable even when the sulfite ion concentration is high that it is difficult to maintain photographic characteristics stable for longer than 3 days.

As the fixing solution, that with a generally used composition can be used. As fixing agents, there can be used thiosulfates, thiocyanates and, in addition, organic sulfur compounds known to exhibit effects as fixing agents. The fixing solution may contain water-soluble aluminum salts or the like as hardener.

The present invention will now be illustrated in more detail by reference to the following Examples.

EXAMPLE 1

To an aqueous gelatin solution maintained at 50° C. were simultaneously added a silver nitrate aqueous solution and a potassium bromide aqueous solution over 30 minutes, during which the pAg was kept at 8.0. Thus, there was prepared a silver bromide emulsion having a mean particle size of 0.22μ. After removal of soluble salts in a conventional manner, this emulsion was chemically ripened at 60° C. for 75 minutes by adding sodium thiosulfate in an amount of 48 mg per mol of silver bromide. This emulsion contained 100 g gelatin per mol of silver bromide. To the resulting silver bromide emulsion was added each of the compounds of the present invention shown in Table 1, comparative compound (a) of 1-formyl-2-p-tolylhydrazide, and comparative compound (b) of 1-formyl-2-(4-acetamidophenyl)hydrazide [from Japanese Patent Application (OPI) No. 16623/78 (corresponding to U.S. Patent Application Ser. No.

967,541 filed on Dec. 7, 1978)] as shown in Table 1 and, further, 5-methylbenzotriazole as an antifoggant, 4-hydroxy-6-methyl-1,3,3a,7-tetrazaindene as a stabilizing agent, a dispersion of polyethyl acrylate for dimensional stability, and 2-hydroxy-4,6-dichloro-1,3,5-triazine sodium salt as a hardener were added thereto, then coated on cellulose triacetate film in a silver amount of 48 mg/100 cm$^2$. Each sample was exposed for 1 second under an optical wedge.

In order to examine changes in photographic properties (sensitivity and gamma) in the effect of changing the degree of stirring the developer, samples were developed for 5 minutes at 20° C. under the following stirring conditions using a developing tank (content volume: 5 l) designed to bubble nitrogen gas from the bottom of the tank so as to stir the developer, then subjected to ordinary processings (stopping, fixing, washing with water, and drying).

No. 5 developed under stirring condition (B) (marked by an asterisk*) as 100.

As is shown in Table 1, when comparative compounds a and b [from Japanese Patent Application (OPI) No. 16623/78 (corresponding to U.S. Patent Application Ser. No. 823,881 filed on Aug. 11, 1977), etc.] were used, sensitivity and gamma varied seriously depending upon the degree of stirring. On the other hand, the use of compounds of the present invention reduced changes in sensitivity and gamma, and good reproducibility of sensitivity and gamma was obtained even when stirring greatly varied. That is, substantially consistent photographic characteristics (sensitivity and gamma) are easily obtained employing any developing process (automatic developing machines based on different stirring methods, dish-developing process, etc.). In addition, the amount of the compound of the present invention is extremely less than that required of comparative compound (a) or (b).

TABLE 1

| Sample No. | Compound | Amount (g/mol AgBr) | Stirring Condition (A) Sensitivity | γ | Stirring Condition (B) Sensitivity | γ | Stirring Condition (C) Sensitivity | γ |
| --- | --- | --- | --- | --- | --- | --- | --- | --- |
| 1 | Comparative Compound (a) | 3.3 | 132 | 20 | 105 | 17 | 72 | 12 |
| 2 | Comparative Compound (b) | 4.8 | 124 | 18 | 100 | 15 | 76 | 12 |
| 3 | (1) | 0.06 | 110 | 20 | 105 | 18 | 105 | 18 |
| 4 | (2) | 0.21 | 78 | 17 | 75 | 15 | 70 | 15 |
| 5 | (5) | 0.07 | 100 | 20 | 100* | 20 | 110 | 20 |
| 6 | (6) | 0.07 | 95 | 20 | 95 | 20 | 98 | 20 |
| 7 | (10) | 0.04 | 105 | 20 | 102 | 19 | 102 | 17 |
| 8 | (12) | 0.43 | 95 | 19 | 98 | 18 | 98 | 18 |
| 9 | (16) | 0.08 | 105 | 19 | 105 | 17 | 110 | 17 |
| 10 | (24) | 0.09 | 108 | 20 | 100 | 18 | 97 | 18 |

*Sensitivity values for stirring condition (B) are determined relative to the sensitivity value for Sample No. 5

Stirring Condition (A)

The system was stirred for 5 seconds from immediately after initiation of the development by introducing the nitrogen steam (flow rate: 200 ml/min), then allowed to stand.

Stirring Condition (B)

The system was stirred for 5 seconds by introducing a nitrogen stream and then allowed to stand for a subsequent 15 seconds. The sequence was repeated alternately for 5 minutes.

Stirring Condition (C)

The system was stirred throughout development. The developer had the following composition.

| Developer | |
| --- | --- |
| N-Methyl-p-aminophenol Hemisulfate | 5 g |
| Hydroquinone | 10 g |
| Anhydrous Sodium Sulfite | 75 g |
| Sodium Metaborate Tetrahydrate | 30 g |
| Polyethylene Glycol (mean molecular weight: 1,500) | 1 g |
| Potassium Hydroxide | 12 g |
| Water to make | 1 l |

The photographic properties thus obtained are shown in Table 1.

In Table 1, relative sensitivities are of reciprocals of exposure amounts necessary to obtain a density of 1.5 excluding fog, and are based using the value of sample

EXAMPLE 2

In manner analogous to Example 1, there were prepared large-sized (30.5 cm × 25.4 cm) samples, and exposed through a 150-line gray contact screen so as to uniformly give 50% dots, followed by developing according to the following two developing processes.

Development I (dish development)

Place 5 l of a developer in a developing dish and develop at 27° C. for 1 minute and 40 seconds with no stirring.

Development II (automatic developing machine)

Develop at 27° C. for 1 minute and 40 seconds using an automatic developing machine, model FG-24 Pakorol, made by Fuji Photo Film Co., Ltd.

The composition of the developer was as follows:

| Developer | |
| --- | --- |
| Hydroquinone | 15 g |
| Anhydrous Sodium Sulfite | 40 g |
| Potassium Carbonate | 70 g |
| Potassium Bromide | 1 g |
| Polyethylene Glycol (mean molecular weight: 1,500) | 1 g |
| 5-Nitroindazole | 30 mg |
| Boric Acid | 8 g |
| Potassium Hydroxide | 18 g |
| Water to make | 1 l |

Unevenness of development was visually rated according to the following four grades A to D.
A: No uneven places were observed.
B: A few uneven places were observed.
C: Many uneven places were observed.
D: Large and many uneven places were observed.

Grades A and B are practically acceptable while grades C and D are practically unacceptable.

As is shown in Table 2, the compounds of the present invention caused almost no unevenness of development both in the processing using the automatic developing machine and in the dish development.

On the other hand, when the comparative compounds were used, unevenness of development was so serious in the dish development that they cannot be practically used, through processing using the automatic developing machine caused unevenness of development within practically acceptable degree.

TABLE 2

| Sample No. | Compound | Automatic Developing Machine | Dish Development |
|---|---|---|---|
| 1 | Comparative Compound (a) | B | C |
| 2 | Comparative Compound (b) | B | C - D |
| 3 | (1) | A | B |
| 5 | (5) | A | A |
| 6 | (6) | A | A |
| 8 | (12) | A | A |
| 10 | (24) | A | A |

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material having at least one silver halide photographic emulsion layer comprising substantially surface latent image type silver halide grains, and containing in said photographic emulsion layer or at least one of other hydrophilic colloid layers a compound represented by the following general formula (I):

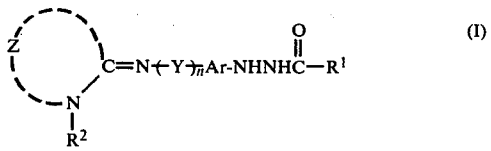

wherein $R^1$ represents a hydrogen atom, an aliphatic group containing only carbon and hydrogen atoms which may be substituted or an aryl group which may be substituted; Ar represents a divalent aryl group which may be substituted; Y represents a divalent linking group containing a carbonamido or a sulfonamido group; n represents 0 or 1; $R^2$ represents a hydrogen atom, an aliphatic group containing only carbon and hydrogen atoms which may be substituted or an aryl group which may be substituted; and Z represents a non-metallic atomic group necessary to form a 5-membered or 6-membered heterocyclic ring together with the

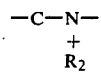

linkage.

2. The photographic light-sensitive material of claim 1, wherein $R^1$ represents a hydrogen atom, an aliphatic group having 1 to 8 carbon atoms which may be substituted or an aromatic group which may be substituted.

3. The photographic light-sensitive material of claim 1, wherein $R^1$ represents a hydrogen atom, an alkyl group having 1 to 8 carbon atoms, an alkenyl group having 2 to 8 carbon atoms, a phenyl group or a naphthyl group, and these groups may be substituted.

4. The photographic light-sensitive material of claims 1, 2 or 3, wherein said substituent is an electron attracting group.

5. The photographic light-sensitive material of claim 4, wherein said electron attracting group includes a halogen atom, a cyano group, a carboxy group and a sulfo group.

6. The photographic light-sensitive material of claim 1, wherein $R^1$ represents a hydrogen atom, a methyl group, an ethyl group, an n-propyl group, an isopropyl group, a trifluoromethyl group, a phenyl group, a 4-chlorophenyl group, a 4-bromophenyl group, a 4-carboxyphenyl group, a 4-sulfophenyl group, a 3,5-dichlorophenyl group, a 2,5-dichlorophenyl group, and a 4-cyanophenyl group.

7. The photographic light-sensitive material of claim 6, wherein $R^1$ represents a hydrogen atom, a methyl group or a substituted or unsubstituted phenyl group.

8. The photographic light-sensitive material of claim 1, wherein $R^1$ represents a hydrogen atom.

9. The photographic light-sensitive material of claim 1, wherein Ar represents a substituted or unsubstituted phenylene group or a substituted or unsubstituted naphthylene group.

10. The photographic light-sensitive material of claim 9, wherein said substituents for said phenylene or naphthylene group includes an alkyl group containing 1 to 20 carbon atoms, a mono- or bi-cyclic aralkyl group containing 1 to 3 carbon atoms in an alkyl moiety thereof, an alkoxy group having 1 to 20 carbon atoms, an amino group mono- or disubstituted by an alkyl group, an aliphatic acylamino group having 2 to 20 carbon atoms, an aromatic acylamino group having 7 to 12 carbon atoms, an alkylthio group having 1 to 12 carbon atoms, and a hydroxy group.

11. The photographic light-sensitive material of claim 1, wherein Ar represents a p-phenylene group.

12. The photographic light-sensitive material of claim 1, wherein $R^2$ represents a straight or branched alkyl group having 1 to 20 carbon atoms which may be substituted, a cycloalkyl group having 3 to 10 carbon atoms which may be substituted, an alkenyl group having 3 to 12 carbon atoms, an alkynyl group having 2 to 10 carbon atoms, or a mono- or bicyclic aryl group having 6 to 10 carbon atoms which may be substituted.

13. The photographic light-sensitive material of claim 1, wherein $R^2$ represents a substituted or unsubstituted aliphatic group containing only carbon and hydrogen atoms.

14. The photographic light-sensitive material of claims 12 or 13, wherein said substituent is a group having up to 15 carbon atoms or no carbon atom.

15. The photographic light-sensitive material of claim 13, wherein said substituent includes an alkoxy group, an aryl group, an aliphatic or aromatic acylamino group, an aliphatic or aromatic acyloxy group, an alkoxycarbonyl group, a mercapto group, a sulfo group or salt thereof, a carboxy group or salt thereof, a hydroxy group, a halogen atom, an amino group, an alkyl substituted amino group, or a carbamoyl group.

16. The photographic light-sensitive material of claim 1, wherein Y represents a —X—R$^3$—CONH— group or a —X—R$^3$—SO$_2$NH—group wherein X represents a divalent aryl group or a saturated or unsaturated divalent aliphatic group containing only carbon and hydrogen atoms and having 1 to 6 carbon atoms; and R$^3$ represents a —A—R$^4$— group wherein A represents —O—, —S—,

or a direct bond, wherein R$^4$ represents a saturated or unsaturated divalent aliphatic group containing only carbon and hydrogen atoms and having 1 to 6 carbon atoms or a direct bond, wherein R$^5$ represents an aliphatic group containing only carbon and hydrogen atoms and having 1 to 6 carbon atoms or an aryl group having 6 to 12 carbon atoms.

17. The photographic light-sensitive material of claim 1, wherein Z comprises a carbon atom, an oxygen atom, a sulfur atom, a selenium atom and/or a nitrogen atom.

18. The photographic light-sensitive material of claim 1, wherein Z represents a thiazoline ring, a benzothiazoline ring, a naphthothiazoline ring, a thiazolidine ring, an oxazoline ring, a benzoxazoline ring, an oxazolidine ring, a selenazoline ring, a benzoselenazoline ring, an imidazoline ring, a benzimidazoline ring, a tetrazoline ring, a triazoline ring, a thiadiazoline ring, an 1,2-dihydropyridine ring, an 1,2-dihydroquinoline ring, an 1,2,3,4-tetrahydroquinoline ring, a perhydro-1,3-oxazine ring, a 2,4-benz[d]oxazine ring, a perhydro-1,3-thiazine ring, a 2,4-benzo[d]thiazine ring, or a uracil ring.

19. The photographic light-sensitive material of claim 1, wherein said substantially surface latent image type silver halide grain is a silver halide which provides a greater sensitivity when developed with development (A) as defined in the specification than when developed by development (B) as defined in the specification.

20. The photographic light-sensitive material of claim 1, wherein said silver halide emulsion is a mono-disperse emulsion.

21. The photographic light-sensitive material of claim 1, wherein said compound of the formula (I) is present in said photographic emulsion layer.

22. The photographic light-sensitive material of claim 1, wherein said compound of the formula (I) is present in an amount of about $10^{-8}$ to $10^{-2}$ mol per mol of silver halide.

23. The photographic light-sensitive material of claim 1, wherein said compound of the formula (I) is present in an amount of about $10^{-6}$ to $10^{-3}$ mol per mol of silver halide.

24. The photographic light-sensitive material of claim 1, wherein said silver halide has a mean particle size of not more than about 0.7 micron and is present in a binder wherein the binder is present in an amount of not more than 250 g per mol of silver halide.

25. The photographic light-sensitive material of claim 1, wherein said silver halide emulsion additionally contains a dispersion of a water-insoluble or slightly soluble synthetic polymer.

26. The photographic light-sensitive material of claim 1, wherein said silver halide emulsion additionally contains an iodide in an amount of about $10^{-4}$ to $10^{-2}$ mol per mol of silver.

27. A process for forming photographic images which comprises developing the photographic light-sensitive material of claim 1 using a developer containing not more than about 0.15 mol per liter sulfite ion and having a pH of about 10.5 to 12.3.

28. A process for forming photographic images which comprises developing the photographic light-sensitive material of claim 1 using a developer containing a dihydroxybenzene.

29. A process for forming photographic images which comprises developing the photographic light-sensitive material of claim 1 in the presence of a polyethylene oxide having a molecular weight of 600 or more.

30. The process for forming photographic images of claim 28, wherein said dihydroxybenzene is used as the sole developing agent.

* * * * *